United States Patent
Fukuda et al.

(10) Patent No.: US 11,452,499 B2
(45) Date of Patent: Sep. 27, 2022

(54) ULTRASOUND DIAGNOSIS APPARATUS AND ULTRASOUND DIAGNOSIS APPARATUS CONTROLLING METHOD

(71) Applicant: CANON MEDICAL SYSTEMS CORPORATION, Otawara (JP)

(72) Inventors: Shogo Fukuda, Sagamihara (JP); Yasuhiko Abe, Otawara (JP); Koichiro Kurita, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 609 days.

(21) Appl. No.: 16/245,496

(22) Filed: Jan. 11, 2019

(65) Prior Publication Data

US 2019/0216427 A1 Jul. 18, 2019

(30) Foreign Application Priority Data

Jan. 15, 2018 (JP) .............................. JP2018-004409

(51) Int. Cl.
*A61B 8/00* (2006.01)
*A61B 8/14* (2006.01)
(Continued)

(52) U.S. Cl.
CPC .......... *A61B 8/4416* (2013.01); *A61B 6/4417* (2013.01); *A61B 6/503* (2013.01);
(Continued)

(58) Field of Classification Search
CPC ..... A61B 8/4416; A61B 8/469; A61B 8/4254; A61B 8/14; A61B 8/483; A61B 6/4417; G06T 7/3337; G06T 2207/10132
See application file for complete search history.

(56) References Cited

U.S. PATENT DOCUMENTS

2009/0097723 A1* 4/2009 Washburn ............. G06T 7/0012
382/128
2013/0226003 A1 8/2013 Edic et al.
(Continued)

FOREIGN PATENT DOCUMENTS

CN 1853572 A 11/2006
CN 104244818 A 12/2014
(Continued)

OTHER PUBLICATIONS

Extended European Search Report dated Aug. 29, 2019 in Patent Application No. 19181386.4, 9 pages.
(Continued)

*Primary Examiner* — Boniface Ngathi N
(74) *Attorney, Agent, or Firm* — Oblon, McClelland, Maier & Neustadt, L.L.P.

(57) ABSTRACT

An ultrasound diagnosis apparatus according to an embodiment includes processing circuitry. The processing circuitry is configured to generate ultrasound images in a time series on the basis of data acquired by transmitting and receiving an ultrasound wave. Every time an ultrasound image satisfying a predetermined condition is generated, the processing circuitry is configured to perform a position aligning process between the ultrasound image satisfying the predetermined condition and a reference image obtained in advance. The processing circuitry is configured to identify, within the ultrasound image satisfying the predetermined condition, a region of interest set in the reference image, on the basis of a result of the position aligning process and to track the region of interest in ultrasound images in a time series that are newly generated by the image generating unit during or after the position aligning process.

9 Claims, 9 Drawing Sheets

(51) Int. Cl.
*A61B 8/08* (2006.01)
*A61B 6/00* (2006.01)
*G06T 7/33* (2017.01)

(52) U.S. Cl.
CPC .............. *A61B 8/0883* (2013.01); *A61B 8/14* (2013.01); *A61B 8/4254* (2013.01); *A61B 8/469* (2013.01); *A61B 8/543* (2013.01); *G06T 7/337* (2017.01); *A61B 8/481* (2013.01); *A61B 8/483* (2013.01); *A61B 8/488* (2013.01); *A61B 8/5246* (2013.01); *G06T 2207/10132* (2013.01)

(56) References Cited

U.S. PATENT DOCUMENTS

| | | |
|---|---|---|
| 2014/0005535 A1 | 1/2014 | Edic et al. |
| 2014/0206994 A1 | 7/2014 | Jain et al. |
| 2014/0330107 A1* | 11/2014 | Shin .................... A61B 8/5223 600/411 |
| 2015/0178921 A1 | 6/2015 | Hashimoto et al. |
| 2015/0257731 A1 | 9/2015 | Abe |
| 2018/0192996 A1 | 7/2018 | Kobayashi et al. |

FOREIGN PATENT DOCUMENTS

| | | | |
|---|---|---|---|
| JP | 2012-245222 | 12/2012 | |
| WO | WO-2018206473 A1 * | 11/2018 | ............. A61B 34/20 |

OTHER PUBLICATIONS

Chinese Office Action dated Mar. 3, 2022, issued in Chinese Patent Application No. 201910025883.4.

Combined Chinese office Action and Search Report dated Jun. 3, 2021 in Patent Application No. 201910025883.4 (with English translation of Category of Cited Documents), 13 pages.

* cited by examiner

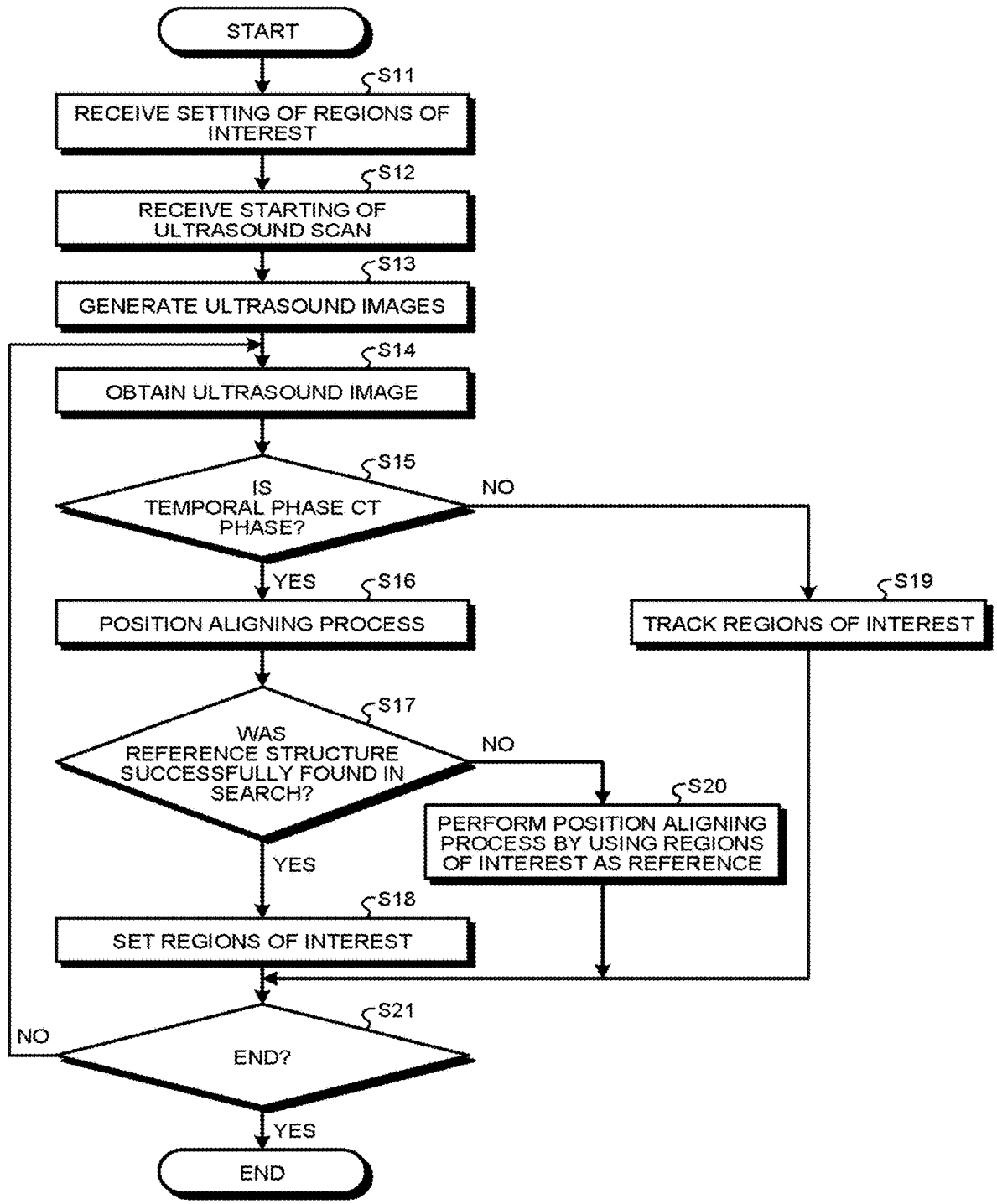

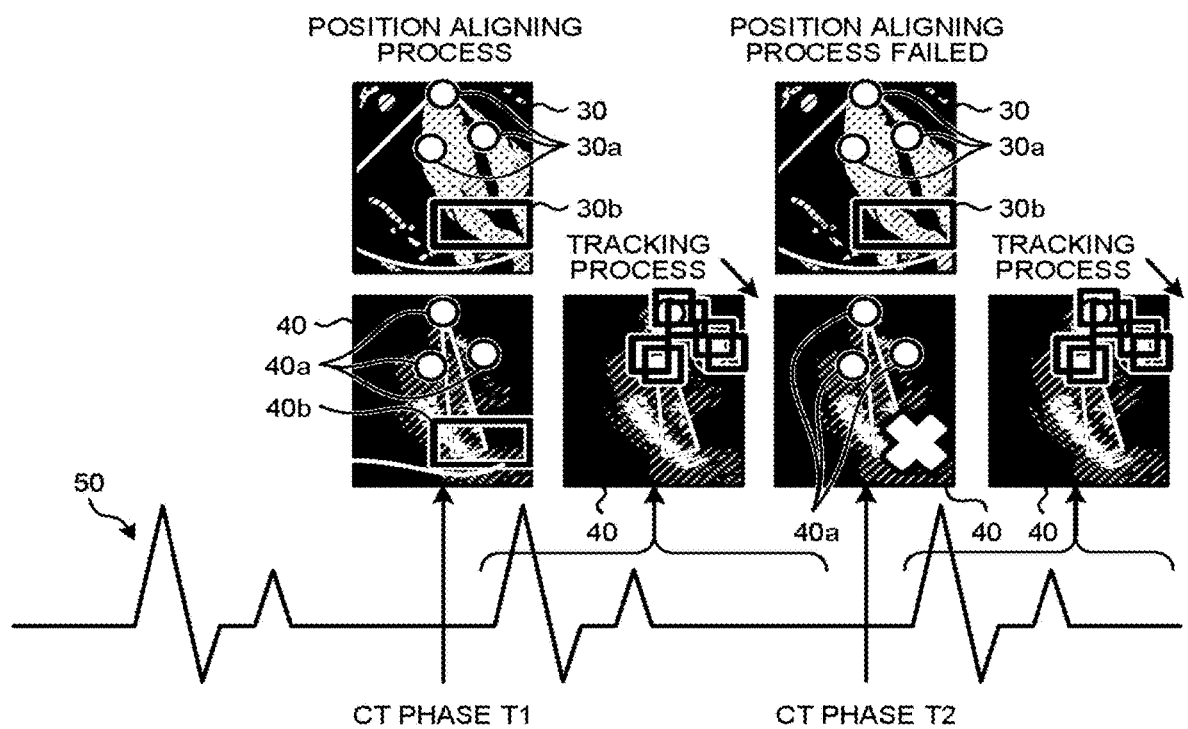

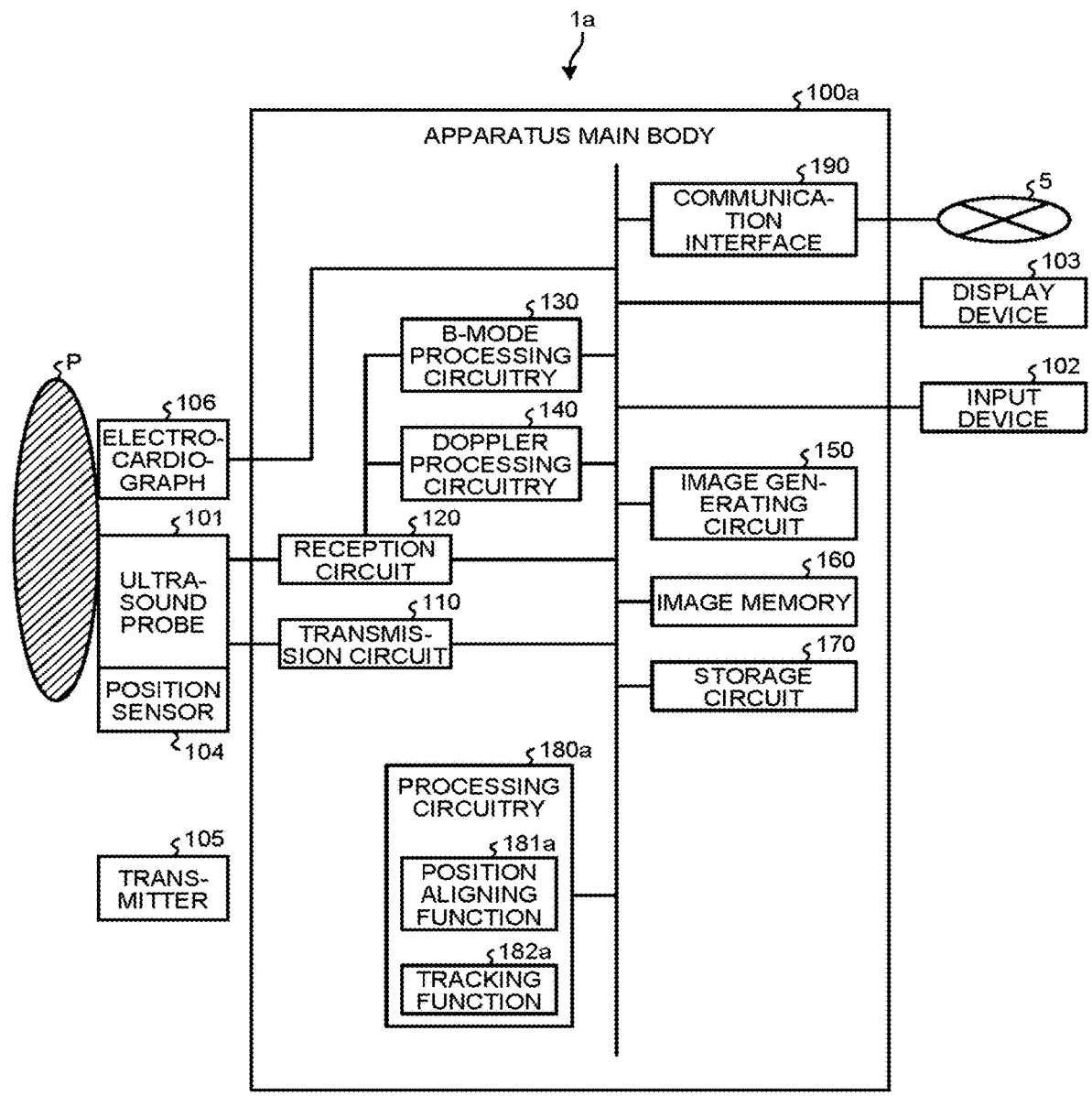

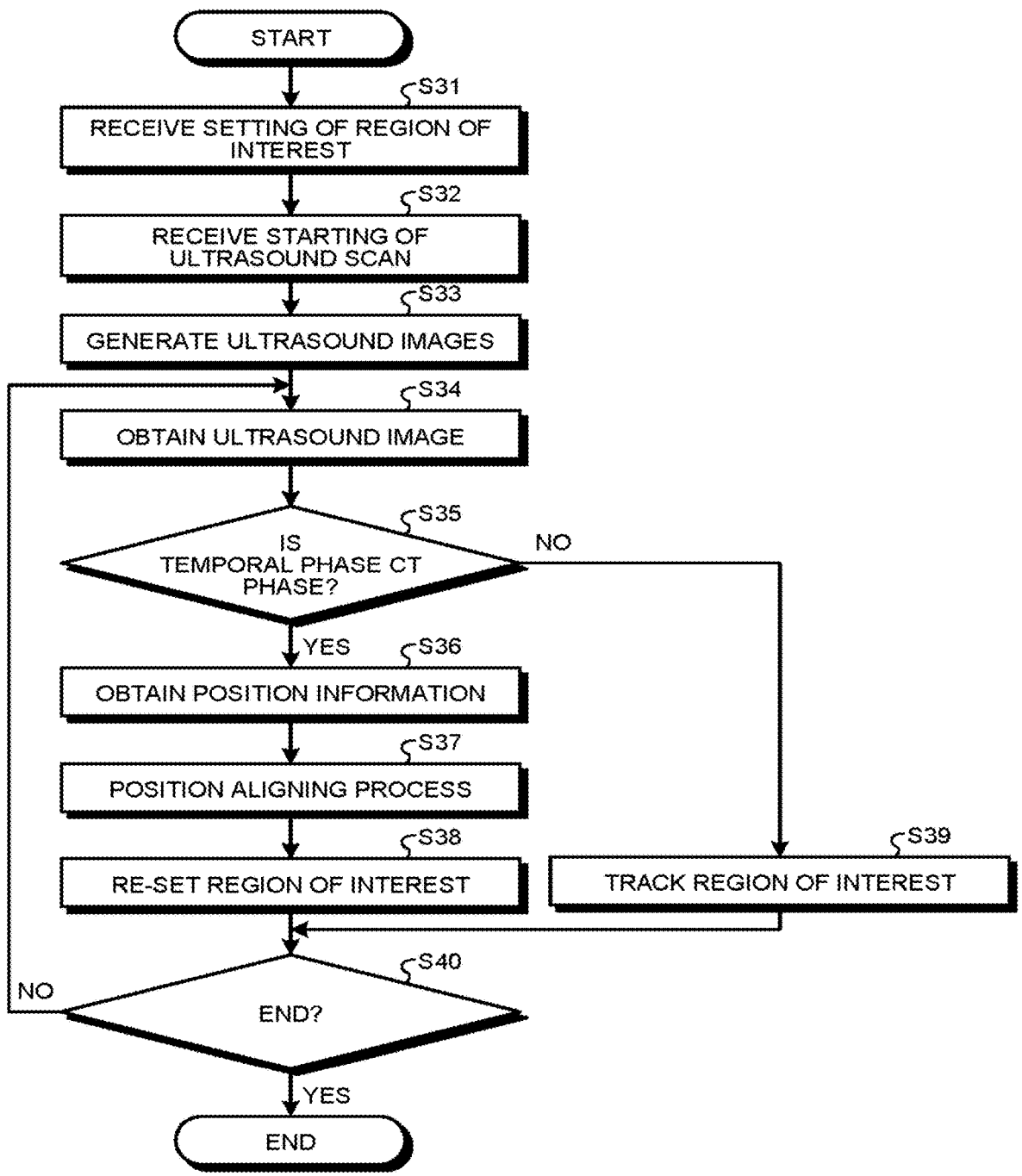

ULTRASOUND DIAGNOSIS APPARATUS AND ULTRASOUND DIAGNOSIS APPARATUS CONTROLLING METHOD

CROSS-REFERENCE TO RELATED APPLICATIONS

This application is based upon and claims the benefit of priority from Japanese Patent Application No. 2018-004409, filed on Jan. 15, 2018; the entire contents of which are incorporated herein by reference.

FIELD

Embodiments described herein related generally to an ultrasound diagnosis apparatus and an ultrasound diagnosis apparatus controlling method.

BACKGROUND

Conventionally, a technique has been known by which a position aligning process is performed between an ultrasound image taken by an ultrasound diagnosis apparatus and a reference image taken by a medical image diagnosis apparatus such as an X-ray Computed Tomography (CT) apparatus. According to this technique, the position aligning process is performed between the ultrasound image and the reference image by, for example, obtaining position information of an ultrasound probe while using a magnetic sensor.

BRIEF DESCRIPTION OF THE DRAWINGS

FIG. 5 is a flowchart illustrating a processing procedure performed by an ultrasound diagnosis apparatus according to a second embodiment;

FIG. 6 is a drawing for explaining the second embodiment;

FIG. 7 is a block diagram illustrating an exemplary configuration of an ultrasound diagnosis apparatus according to a third embodiment; and FIG. 8 is a flowchart illustrating a processing procedure performed by the ultrasound diagnosis apparatus according to the third embodiment.

DETAILED DESCRIPTION

An ultrasound diagnosis apparatus according to an embodiment includes processing circuitry. The processing circuitry is configured to generate ultrasound images in a time series on the basis of data acquired by transmitting and receiving an ultrasound wave. Every time an ultrasound image satisfying a predetermined condition is generated, the processing circuitry is configured to perform a position aligning process between the ultrasound image satisfying the predetermined condition and a reference image obtained in advance. The processing circuitry is configured to identify, within the ultrasound image satisfying the predetermined condition, a region of interest set in the reference image, on the basis of a result of the position aligning process and to track the region of interest in ultrasound images in a time series that are newly generated by the image generating unit during or after the position aligning process.

Exemplary embodiments of an ultrasound diagnosis apparatus and an ultrasound diagnosis apparatus controlling method will be explained below, with reference to the accompanying drawings. Possible embodiments are not limited to the embodiments described below. Further, the description of each of the embodiments is, in principle, similarly applicable to any other embodiment.

First Embodiment

Figure 1:
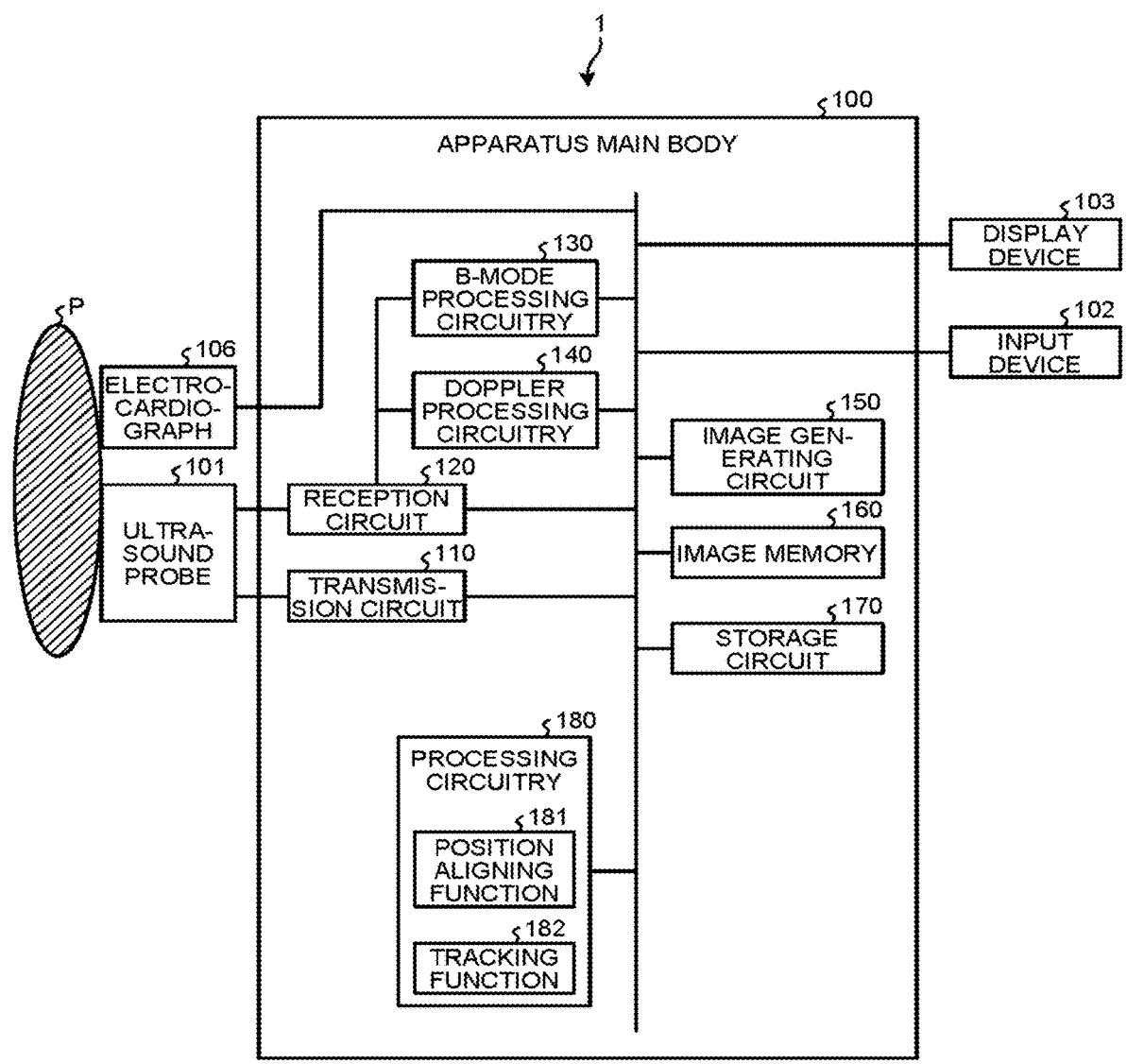
FIG. 1 is a block diagram illustrating an exemplary configuration of an ultrasound diagnosis apparatus according to a first embodiment.

FIG. 1 is a block diagram illustrating an exemplary configuration of an ultrasound diagnosis apparatus 1 according to a first embodiment. As illustrated in FIG. 1, the ultrasound diagnosis apparatus 1 according to the first embodiment includes an apparatus main body 100, an ultrasound probe 101, an input device 102, and a display device 103. The ultrasound probe 101, the input device 102, and the display device 103 are each connected to the apparatus main body 100.

The ultrasound probe 101 includes a plurality of transducer elements (piezoelectric transducer elements). The ultrasound probe 101 is brought into contact with the body surface of an examined subject (hereinafter "patient") P and is configured to transmit and receive an ultrasound wave (to perform an ultrasound scan). The plurality of transducer elements are configured to generate an ultrasound wave on the basis of a drive signal supplied thereto from a transmission circuit 110 (explained later) included in the apparatus main body 100. The generated ultrasound wave is reflected on a plane of unmatched acoustic impedance in the body of the patient P and is received by the plurality of transducer elements as reflected-wave signals (reception echo) including a component scattered by a scattering member in a tissue, and the like. The ultrasound probe 101 is configured to send the reflected-wave signals received by the plurality of transducer elements to a reception circuit 120.

In the present embodiment, an example will be explained in which the ultrasound probe 101 is a two-dimensional ultrasound probe (which may be referred to as a "2D array probe") including the plurality of transducer elements arranged in a matrix formation (a grid formation); however, possible embodiments are not limited to this example. For instance, the ultrasound probe 101 may be a one-dimensional ultrasound probe (which may be referred to as a "1D array probe") including the plurality of transducer elements one-dimensionally arranged in a predetermined direction.

The input device 102 includes a mouse, a keyboard, a button, a panel switch, a touch command screen, a foot switch, a trackball, a joystick, and/or the like. The input device 102 is configured to receive various types of setting requests from an operator of the ultrasound diagnosis apparatus 1 and to transfer the received various types of setting requests to the apparatus main body 100. For example, the input device 102 is configured to receive, from the operator, an instruction to set a Region Of Interest (ROI) in an image displayed on the display device 103.

The display device 103 is configured to display a Graphical User Interface (GUI) used by the operator of the ultrasound diagnosis apparatus 1 to input the various types of setting requests through the input device 102 and to display ultrasound image data generated by the apparatus main body 100 and the like. For example, the display device 103 is configured by using a liquid crystal display device, a Cathode Ray Tube (CRT) display device, or the like. Further, the display device 103 may be referred to as a monitor, as appropriate.

The apparatus main body 100 is an apparatus configured to generate the ultrasound image data on the basis of the reflected-wave signals received by the ultrasound probe 101. As illustrated in FIG. 1, the apparatus main body 100 includes, for example, the transmission circuit 110, the reception circuit 120, B-mode processing circuitry 130, Doppler processing circuitry 140, an image generating circuit 150, an image memory 160, a storage circuit 170, and processing circuitry 180. The transmission circuit 110, the reception circuit 120, the B-mode processing circuitry 130, the Doppler processing circuitry 140, the image generating circuit 150, the image memory 160, the storage circuit 170, and the processing circuitry 180 are connected so as to be able to communicate with one another.

The transmission circuit 110 includes a pulser circuit and the like. The pulser circuit is configured to repeatedly generate a rate pulse used for forming a transmission ultrasound wave at a predetermined rate frequency (called a Pulse Repetition Frequency [PRF]) and to output the generated rate pulses to the ultrasound probe 101. Further, the pulser circuit is configured to apply the drive signal (a drive pulse) to the ultrasound probe 101 with timing based on the rate pulses.

Further, under control of the processing circuitry 180, the transmission circuit 110 is configured to output an amplitude value of the drive signal output by the pulser circuit. Further, under control of the processing circuitry 180, the transmission circuit 110 is configured to transmit a delay amount to be applied to the ultrasound wave transmitted from the ultrasound probe 101, to the ultrasound probe 101.

The reception circuit 120 includes an Analog/Digital (A/D) converter and a reception beam former. When the reception circuit 120 has received the reflected-wave signals output from the ultrasound probe 101, the A/D converter at first converts the reflected-wave signals into digital data, so that the reception beam former generates reflected-wave data by performing a phased adding process on pieces of digital data from channels and further transmits the generated reflected-wave data to the B-mode processing circuitry 130 and the Doppler processing circuitry 140.

The B-mode processing circuitry 130 is configured to receive the reflected-wave data output from the reception circuit 120 and to generate data (B-mode data) in which signal intensities are expressed by degrees of brightness, by performing a logarithmic amplification process, an envelope detection process, and/or the like on the received reflected-wave data.

The Doppler processing circuitry 140 is configured to receive the reflected-wave data output from the reception circuit 120 and to generate data (Doppler data) obtained by extracting moving member information such as average velocity, dispersion, power, and the like with respect to multiple points, by performing a frequency analysis to obtain velocity information from the received reflected-wave data and extracting blood flows, tissues, contrast agent echo components based on the Doppler effect.

The image generating circuit 150 is configured to generate the ultrasound image data from the data generated by the B-mode processing circuitry 130 and the Doppler processing circuitry 140. For example, the image generating circuit 150 is configured to generate B-mode image data in which intensities of the reflected waves are expressed with degrees of brightness, from the B-mode data generated by the B-mode processing circuitry 130. Further, for example, the image generating circuit 150 is configured to generate Doppler image data expressing the moving member information, from the Doppler data generated by the Doppler processing circuitry 140. The Doppler image data may be velocity image data, dispersion image data, power image data, or image data combining any of these types of image data.

In this situation, generally speaking, the image generating circuit 150 converts (by performing a scan convert process) a scanning line signal sequence from an ultrasound scan into a scanning line signal sequence in a video format used by, for example, television and generates display-purpose ultrasound image data. More specifically, the image generating circuit 150 generates the display-purpose ultrasound image data by performing a coordinate transformation process compliant with the ultrasound scan mode used by the ultrasound probe 101. Further, as various types of image processing processes besides the scan convert process, the image generating circuit 150 performs, for example, an image processing process (a smoothing process) to re-generate a brightness average value image, an image processing process (an edge enhancement process) that uses a differential filter inside an image, or the like, by using a plurality of image frames resulting from the scan convert process. Also, the image generating circuit 150 combines text information of various parameters, scale graduations, body marks, and the like, with the ultrasound image data.

The image memory 160 is a memory configured to store therein the image data (the B-mode image data, the Doppler image data, and the like) generated by the image generating circuit 150. Further, the image memory 160 is also capable of storing therein any of the data generated by the B-mode processing circuitry 130 and the Doppler processing circuitry 140. For example, the operator is able to invoke any of the B-mode data and the Doppler data stored in the image memory 160. The invoked B-mode data and Doppler data can serve as the display-purpose ultrasound image data after being routed through the image generating circuit 150.

The storage circuit 170 is configured to store therein control programs for performing ultrasound transmissions and receptions, image processing processes, and display processes as well as various types of data such as diagnosis information (e.g., patients' IDs, medical doctors' observations), diagnosis protocols, various types of body marks, and the like. Further, the storage circuit 170 may be used, as necessary, for saving therein any of the image data stored in the image memory 160, and the like. Further, the data stored in the storage circuit 170 may be transferred to an external apparatus via a communication interface (not illustrated).

The processing circuitry 180 is configured to control overall processes performed by the ultrasound diagnosis apparatus 1. More specifically, the processing circuitry 180 is configured to control processes performed by the transmission circuit 110, the reception circuit 120, the B-mode processing circuitry 130, the Doppler processing circuitry 140, the image generating circuit 150 and the like, on the basis of the various types of setting requests input thereto by the operator via the input device 102 and the various types of control programs and the various types of data read from the storage circuit 170. Further, the processing circuitry 180 is configured to cause the display device 103 to display the ultrasound image data stored in the image memory 160.

Further, as illustrated in FIG. 1, the processing circuitry 180 is configured to perform a position aligning function 181 and a tracking function 182. In this situation, for example, processing functions executed by the constituent elements of the processing circuitry 180 illustrated in FIG. 1, namely, the position aligning function 181 and the tracking function 182, are each recorded in the storage circuit 170 in the form of a computer-executable program. The processing circuitry 180 is a processor configured to realize the functions corresponding to the programs by reading and executing the programs from the storage circuit 170. In other words, the processing circuitry 180 that has read the programs has the functions illustrated within the processing circuitry 180 in FIG. 1. Processes performed by the position aligning function 181 and the tracking function 182 will be explained later.

In this situation, the transmission circuit 110, the reception circuit 120, the B-mode processing circuitry 130, the Doppler processing circuitry 140, the image generating circuit 150, and the processing circuitry 180 built in the apparatus main body 100 are configured by using hardware such as a processor (a Central Processing Unit [CPU], a Micro-Processing Unit [MPU], an integrated circuit, or the like).

Further, as illustrated in FIG. 1, the ultrasound diagnosis apparatus 1 according to the first embodiment is connected to an electrocardiograph 106. The electrocardiograph 106 is a device configured to detect an electrocardiographic signal of the patient P. For example, as a biological signal of the patient P on whom an ultrasound scan is performed, the electrocardiograph 106 obtains an electrocardiogram (ECG) of the patient P. The electrocardiograph 106 transmits the obtained electrocardiogram to the apparatus main body 100. The electrocardiographic signal detected by the electrocardiograph 106 is stored into the storage circuit 170 while being kept in correspondence with image taking times of ultrasound image data (the times over which an ultrasound scan was performed to generate the ultrasound image data). As a result, frames of the acquired ultrasound image data are kept in correspondence with cardiac phases of the patient P.

Figure 2:
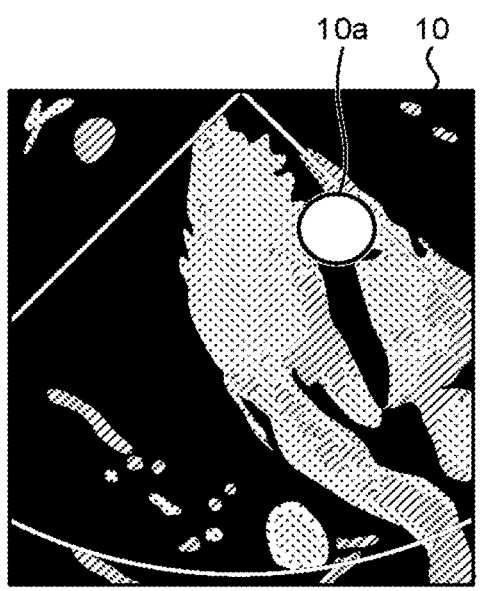
FIG. 2 is a drawing for explaining a position aligning process performed between an ultrasound image and a reference image by implementing a magnetic sensor method.
Figure 2:
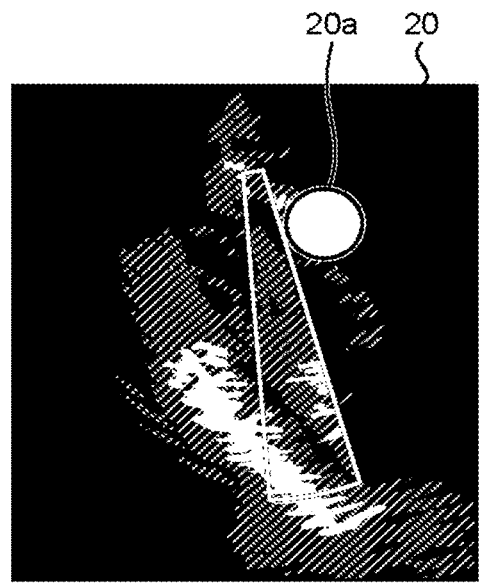

The ultrasound diagnosis apparatus 1 structured as described above is configured to perform a position aligning process between an ultrasound image generated in a real-time manner by performing an ultrasound scan and a reference image taken by a medical image diagnosis apparatus such as an X-ray Computed Tomography (CT) apparatus. In this situation, for example, the ultrasound diagnosis apparatus 1 may perform the position aligning process between the ultrasound image and the reference image by recognizing a structure of the heart. In that situation, it is possible to use a method (hereinafter, "magnetic sensor method") by which the position aligning process is performed between the ultrasound image and the reference image, by obtaining position information of the ultrasound probe 101 while using a magnetic sensor. FIG. 2 is a drawing for explaining the position aligning process performed between an ultrasound image and a reference image by implementing the magnetic sensor method.

In FIG. 2, a reference image 10 taken by an X-ray CT apparatus is illustrated on the left-hand side, whereas an ultrasound image 20 taken by the ultrasound diagnosis apparatus 1 is illustrated on the right-hand side. The reference image 10 illustrated in FIG. 2 is an image taken in a periodical reference temporal phase. Further, the example in FIG. 2 illustrates the ultrasound image 20 taken in a temporal phase different from the temporal phase in which the reference image 10 was taken. In other words, in the example in FIG. 2, the temporal phase in which the reference image 10 was taken is not the same as the temporal phase in which the ultrasound image 20 was taken. Hereinafter, the temporal phase in which the reference image 10 was taken may be referred to as a CT phase.

As illustrated in FIG. 2, in the reference image 10, an observation-purpose region of interest 10a is set with an observation target. In this situation, according to the magnetic sensor method illustrated in FIG. 2, the position aligning process is performed between the ultrasound image 20 taken in the same temporal phase as that of the reference image 10 and the reference image 10, by obtaining the position information of the ultrasound probe 101 while using the magnetic sensor. Further, in the ultrasound image 20 taken in the same temporal phase as that of the reference image 10, an observation-purpose region of interest 20a corresponding to the observation-purpose region of interest 10a is set.

However, according to this method, in the ultrasound image 20, a position shift due to the heartbeats occurs to the observation-purpose region of interest 20a corresponding to the observation-purpose region of interest 10a set in the reference image 10. For example, as illustrated in the ultrasound image 20 on the right-hand side of FIG. 2, the observation-purpose region of interest 20a does not move from the position thereof within the ultrasound image 20 taken in the same temporal phase as that of the reference image 10. For this reason, the position in which the observation-purpose region of interest 20a is set is different from the actual position subject to the observation.

Further, the position aligning process using the magnetic sensor has not been realized with Transesophageal Echocardiography (TEE) probes. In other words, it is not possible to apply the magnetic sensor method to TEE probes. For this reason, when a position aligning process is performed by recognizing a structure of the heart in an ultrasound image taken by a TEE probe, the position aligning process itself becomes impossible when the structure of the heart used as a reference in the position aligning process comes out of the image taking region. In that situation, it also becomes impossible to display the observation target of interest, in the ultrasound image.

To cope with this situation, the ultrasound diagnosis apparatus 1 according to the first embodiment is configured to perform the position aligning process between the reference image and the ultrasound image by recognizing a structure of the heart in the reference image and the ultrasound image. Subsequently, the ultrasound diagnosis apparatus 1 according to the first embodiment is configured to set, within the ultrasound image, an observation-purpose region of interest designated in the reference image, on the basis of a relative positional relationship based on the structure of the heart. After that, the ultrasound diagnosis apparatus 1 according to the first embodiment is configured to perform a position aligning process once and to subsequently display a moving image by tracking the observation-purpose region of interest in ultrasound images in a real-time manner.

Further, the ultrasound diagnosis apparatus 1 according to the first embodiment is configured to recognize, in the CT phase, the structure of the heart in an ultrasound image through an ECG-based synchronization and to perform a position aligning process and to re-set an observation-purpose region of interest again. For example, every time an ultrasound image in the CT phase is generated at each heartbeat, the ultrasound diagnosis apparatus 1 according to the first embodiment is configured to perform a position aligning process between the ultrasound image and the reference image by recognizing the structure of the heart in the ultrasound image.

Further, when being unable to recognize, in the CT phase, the structure in any of the ultrasound images, the ultrasound diagnosis apparatus 1 according to the first embodiment is configured to keep tracking the observation-purpose region of interest, without re-setting the observation-purpose region of interest.

These processes are realized as a result of the processing circuitry 180 executing the position aligning function 181 and the tracking function 182. For example, every time an ultrasound image satisfying a predetermined condition is generated by the image generating circuit 150, the position aligning function 181 is configured to perform a position aligning process between the ultrasound image satisfying the predetermined condition and a reference image obtained in advance. In this situation, the ultrasound image satisfying the predetermined condition is an ultrasound image corresponding to a periodical reference temporal phase. Further, the periodical reference temporal phase is a temporal phase in which the reference image was taken.

On the basis of a result of the position aligning process, the tracking function 182 is configured to identify, within the ultrasound image satisfying the predetermined condition, the observation-purpose region of interest set in the reference image and to further track the observation-purpose region of interest in ultrasound images generated in a time series by the image generating circuit 150 during or after the position aligning process.

Figure 3:
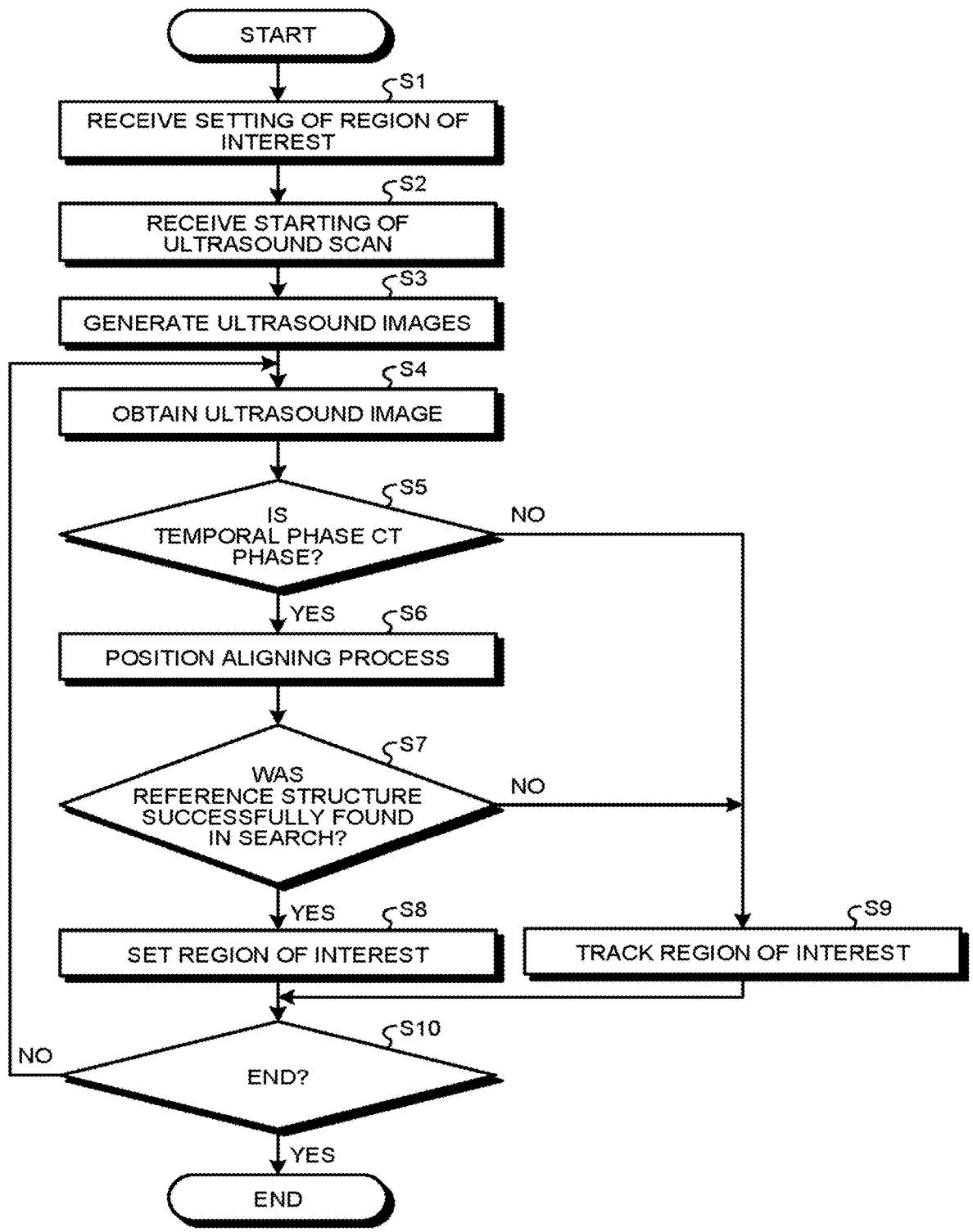
FIG. 3 is a flowchart illustrating a processing procedure performed by the ultrasound diagnosis apparatus according to the first embodiment.

FIG. 3 is a flowchart illustrating a processing procedure performed by the ultrasound diagnosis apparatus 1 according to the first embodiment. FIGS. 4A to 4D are drawings for explaining the first embodiment. With reference to FIG. 3, while the flowchart explains an operation performed by the entirety of the ultrasound diagnosis apparatus 1, the following will explain which step in the flowchart corresponds to each of the constituent elements.

Steps S1 and S2 are steps realized by the input device 102. At step S1, the input device 102 receives a setting of an observation-purpose region of interest. In the present example, an X-ray CT image taken by an X-ray CT apparatus in a reference temporal phase will be used as a reference image. For example, the X-ray CT image serving as the reference image is a two-dimensional image generated from three-dimensional volume data acquired by the X-ray CT apparatus. As illustrated on the left-hand side of FIG. 4A, the display device 103 is displaying a reference image 30. Further, within the reference image 30 displayed on the display device 103, the input device 102 receives, from the operator, the setting of an observation-purpose region of interest 30*a*.

At step S2, the input device 102 receives starting of an ultrasound scan. Accordingly, the processing circuitry 180 causes the ultrasound scan to be executed by controlling the transmission circuit 110 and the reception circuit 120. With reference to FIG. 3, an example will be explained in which the ultrasound scan is performed by using the heart as an examined site.

Step S3 is a step realized by the image generating circuit 150. At step S3, the image generating circuit 150 generates ultrasound images. For example, on the basis of data acquired by transmitting and receiving an ultrasound wave, the image generating circuit 150 generates the ultrasound images in a time series. In the following sections, an example will be explained in which the image generating circuit 150 generates two-dimensional ultrasound images.

Steps S4 through S7 and S10 are steps corresponding to the position aligning function 181. Steps S4 through S7 and S10 are steps at which the position aligning function 181 is realized as a result of the processing circuitry 180 invoking and executing a predetermined program corresponding to the position aligning function 181 from the storage circuit 170. At step S4, the position aligning function 181 obtains an ultrasound image.

At step S5, the position aligning function 181 judges whether or not the temporal phase of the ultrasound image obtained at step S4 is the CT phase. In this situation, the position aligning function 181 obtains the cardiac phase kept in correspondence with the ultrasound image obtained at step S4 and judges whether or not the obtained cardiac phase is the same as the cardiac phase in which the reference image was taken. When the cardiac phase kept in correspondence with the ultrasound image is the same as the cardiac phase in which the reference image was taken, the position aligning function 181 determines that the temporal phase of the ultrasound image is the CT phase. In this situation, when having determined that the obtained temporal phase of the ultrasound image is not the CT phase (step S5: No), the position aligning function 181 proceeds to step S9.

On the contrary, when having determined that the obtained temporal phase of the ultrasound image is the CT phase (step S5: Yes), the position aligning function 181 performs a position aligning process (step S6). The reference image 30 is illustrated on the left-hand side of FIG. 4B. Further, in FIG. 4B, the observation-purpose region of interest 30*a* is set in the reference image 30. An ultrasound image 40 is illustrated on the right-hand side of FIG. 4B. The cardiac phase kept in correspondence with the ultrasound image 40 is the same as the cardiac phase in which the reference image 30 was taken. In this situation, for example, the position aligning function 181 performs the position aligning process between the ultrasound image 40 in the CT phase and the reference image 30, by searching for a reference structure included in the reference image 30 from the ultrasound image 40 in the CT phase. In this situation, the reference structure is a site that is not impacted by heartbeats and may be a valve annulus or the left auricle, for example.

Figure 4A:
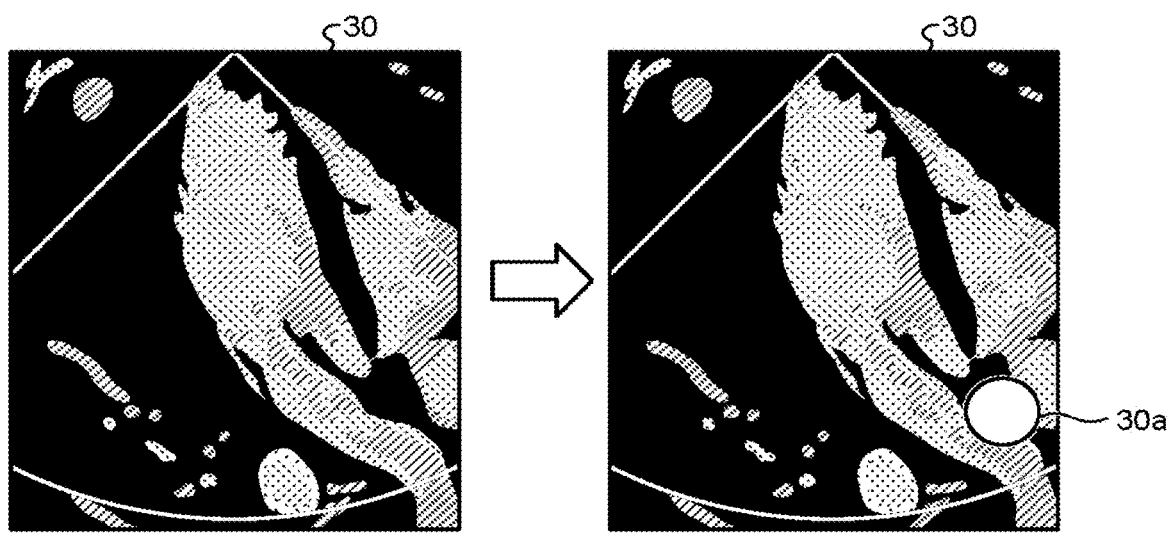
FIG. 4A is a drawing for explaining the first embodiment.
Figure 4B:
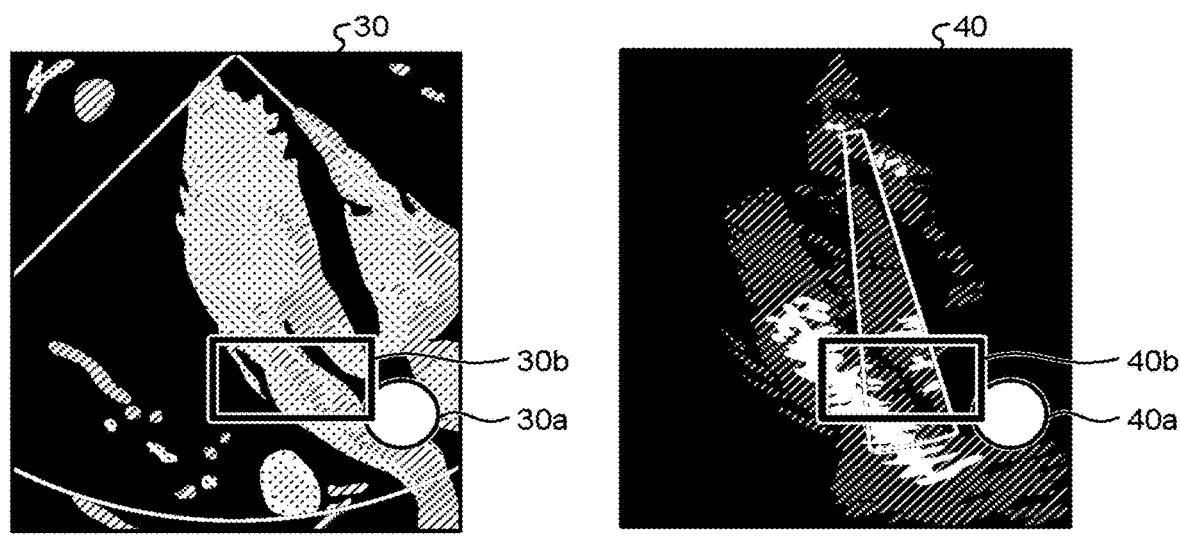
FIG. 4B is another drawing for explaining the first embodiment.

More specifically, within the reference image 30 illustrated in FIG. 4B, the position aligning function 181 sets a region including the reference structure as a position-aligning-purpose reference region 30*b*. After that, the position aligning function 181 searches for a region corresponding to the position-aligning-purpose reference region 30*b* from the ultrasound image 40 illustrated in FIG. 4B. The example in FIG. 4B illustrates a situation where, within the ultrasound image 40, the position aligning function 181 has identified a position-aligning-purpose reference region 40*b* corresponding to the position-aligning-purpose reference region 30*b*.

At step S7, the position aligning function 181 judges whether or not the reference structure was successfully found in the search. For example, as illustrated on the right-hand side of FIG. 4B, when having identified the position-aligning-purpose reference region 40*b* corresponding to the position-aligning-purpose reference region 30*b*, the position aligning function 181 determines that the reference structure was successfully found in the search.

In this situation, when determining that the reference structure was successfully found in the search (step S7: Yes), the position aligning function 181 proceeds to step S8. On the contrary, when having determined that the reference structure was not successfully found in the search (step S7: No), the position aligning function 181 proceeds to step S9.

Steps S8 and S9 are steps corresponding to the tracking function 182. Steps S8 and S9 are steps at which the tracking function 182 is realized as a result of the processing circuitry 180 invoking and executing a predetermined program corresponding to the tracking function 182 from the storage circuit 170. At step S8, the tracking function 182 sets an observation-purpose region of interest in the ultrasound image.

For example, on the basis of a result of the position aligning process at step S6, the tracking function 182 identifies and sets, within the ultrasound image in the CT phase, the observation-purpose region of interest that was set in the reference image. More specifically, as illustrated on the right-hand side of FIG. 4B, within the ultrasound image 40, the tracking function 182 identifies and sets an observation-purpose region of interest 40a corresponding to the observation-purpose region of interest 30a that was set in the reference image 30, on the basis of the relative positional relationship based on the structure of the heart.

Figure 4C:
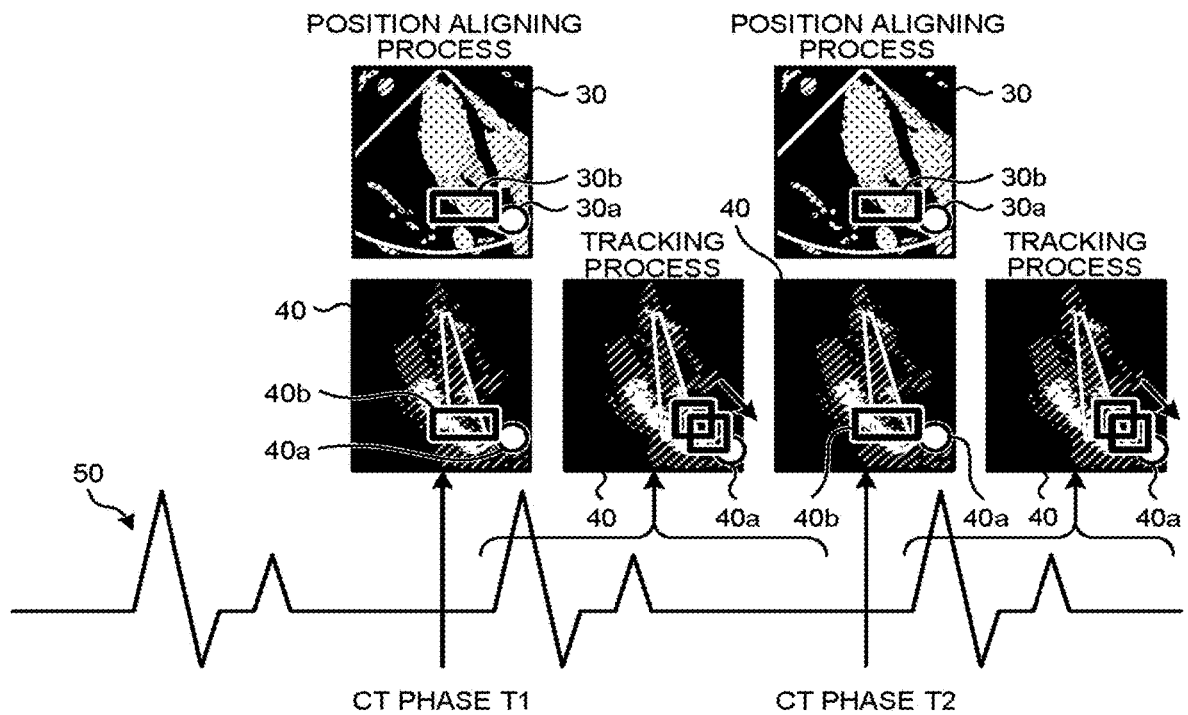
FIG. 4C is yet another drawing for explaining the first embodiment.

In this situation, every time an ultrasound image in the CT phase is generated, the tracking function 182 identifies, within the ultrasound image 40, an observation-purpose region of interest 40a corresponding to the observation-purpose region of interest 30a that was set in the reference image 30. FIG. 4C illustrates a plurality of ultrasound images 40 generated in a time series and an electrocardiographic waveform 50. Further, FIG. 4C illustrates the reference image 30 in the CT phase. For example, as illustrated in FIG. 4C, at a time T1 in the CT phase, the tracking function 182 sets the observation-purpose region of interest 40a in the ultrasound image 40, on the basis of the relative positional relationship based on the structure of the heart. After that, at a time T2 in the CT phase, the tracking function 182 re-sets the observation-purpose region of interest 40a in the ultrasound image 40, on the basis of the relative positional relationship based on the structure of the heart.

At step S9, the tracking function 182 tracks the observation-purpose region of interest. For example, the tracking function 182 tracks the observation-purpose region of interest in the ultrasound images in the time series that are newly generated by the image generating circuit 150 during or after the position aligning process. In this situation, the tracking function 182 tracks the observation-purpose region of interest by implementing a speckle tracking method or the like, for example.

As explained above, when it is determined at step S5 that the phase is not the CT phase or when the reference structure was not successfully found in the search at step S7, the tracking function 182 tracks the observation-purpose region of interest. For example, when it is determined at step S5 that the phase is not the CT phase, the tracking function 182 tracks the observation-purpose region of interest during the time period from the time T1 in the CT phase to the time T2 in the CT phase illustrated in FIG. 4C. Further, the tracking function 182 similarly tracks the observation-purpose region of interest during the time period from the time T2 in the CT phase illustrated in FIG. 4C to the subsequent time in the CT phase.

Figure 4D:
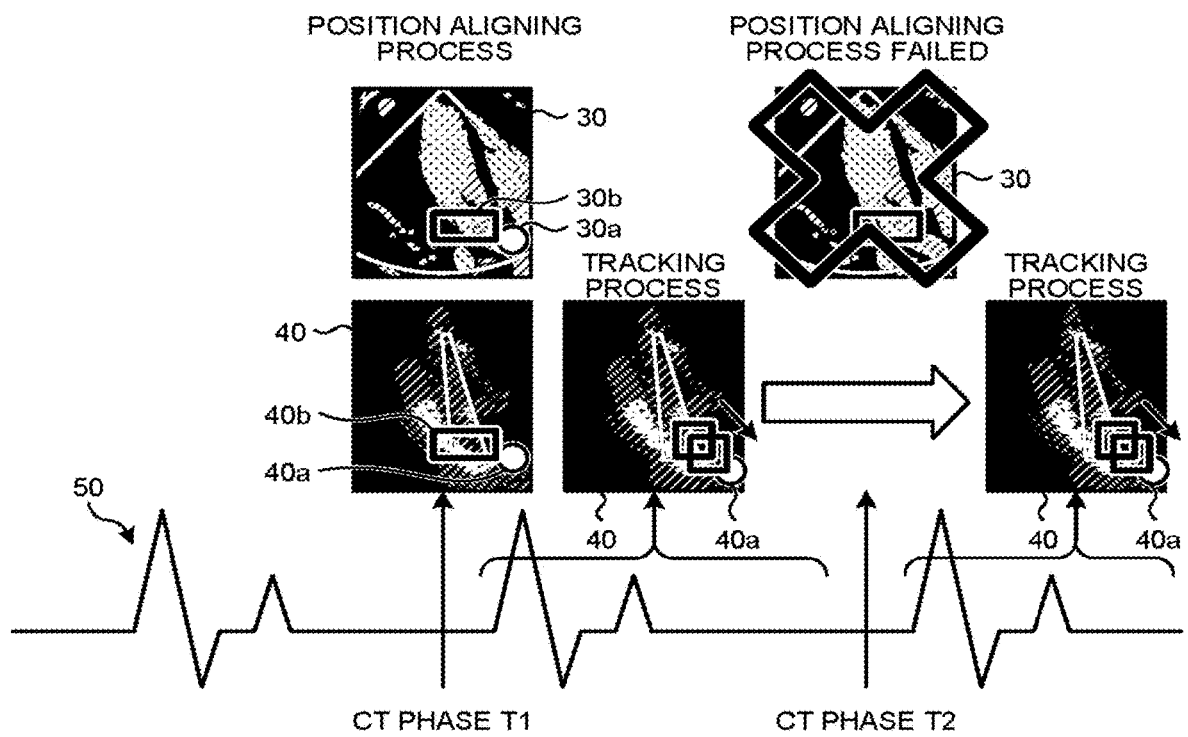
FIG. 4D is yet another drawing for explaining the first embodiment.

Further, for example, when the reference structure was not successfully found in the search at step S7, the tracking function 182 keeps tracking the observation-purpose region of interest. FIG. 4D illustrates a plurality of ultrasound images 40 generated in a time series and the electrocardiographic waveform 50. Further, FIG. 4D illustrates reference image 30 in the CT phase. For example, as illustrated in FIG. 4D, at the time T1 in the CT phase, the tracking function 182 sets the observation-purpose region of interest 40a in the ultrasound image 40, on the basis of the relative positional relationship based on the structure of the heart. After that, at the time of re-setting the observation-purpose region of interest 40a at the time T2 in the CT phase, when the reference structure is not successfully found and the position aligning process has failed, the tracking function 182 tracks the observation-purpose region of interest 40a. In other words, when the reference structure is not successfully found in the search, the tracking function 182 keeps tracking the observation-purpose region of interest in the ultrasound images in the time series that are newly generated by the image generating circuit 150 during or after the position aligning process.

At step S10, the position aligning function 181 judges whether or not an ending process has been received. In this situation, for example, when having received, from the operator, an ending of the ultrasound scan via the input device 102 (step S10: Yes), the position aligning function 181 ends the process. On the contrary, when determining that an ending has not been received (step S10: No), the position aligning function 181 returns to step S4 where a newly-generated ultrasound image is obtained.

As explained above, the ultrasound diagnosis apparatus 1 according to the first embodiment is configured to perform, in the CT phase, the position aligning process between the reference image and the ultrasound image, to set the observation-purpose region of interest, and to track the observation-purpose region of interest at the times other than those in the CT phase. As a result, according to the first embodiment, in the temporal phases other than the CT phase, it is possible to observe the observation-purpose region of interest that was set prior to the manipulation, in a real-time manner in synchronization with the movement of the heart.

Further, in the CT phase, the ultrasound diagnosis apparatus 1 according to the first embodiment is configured to re-set the observation-purpose region of interest. As a result, according to the first embodiment, it is possible to reset position error, if any, that may be caused by the tracking of the observation-purpose region of interest.

Further, the ultrasound diagnosis apparatus 1 according to the first embodiment is configured to track the observation-purpose region of interest, even when being unable to perform the position aligning process between the reference image and the ultrasound image, because, in the CT phase, the reference structure used as a reference in the position aligning process comes out of the image taking area of the ultrasound image. With this arrangement, according to the first embodiment, it is possible to display the observation-purpose region of interest.

Second Embodiment

In the first embodiment described above, the example is explained in which the observation-purpose region of interest keeps being tracked in the newly-generated ultrasound images in the time series, when the structure of the heart is not successfully found in the search from the ultrasound image in the CT phase. In a second embodiment, an example will be explained in which, when the structure of the heart is not successfully found in the search from an ultrasound image in the CT phase, a position aligning process is performed between an ultrasound image in the CT phase and a reference image, by using observation-purpose regions of interest.

An exemplary configuration of the ultrasound diagnosis apparatus 1 according to the second embodiment is the same as the configuration of the ultrasound diagnosis apparatus 1 according to the first embodiment illustrated in FIG. 1, except that a part of the functions of the position aligning function 181 is different. When the reference structure is not successfully found in the search, the position aligning function 181 according to the second embodiment is configured to perform the position aligning process between an ultrasound image in the CT phase and the reference image, by using the observation-purpose regions of interest.

FIG. 5 is a flowchart illustrating a processing procedure performed by the ultrasound diagnosis apparatus 1 according to the second embodiment. FIG. 6 is a drawing for explaining the second embodiment. With reference to FIG. 5, while the flowchart explains an operation performed by the entirety of the ultrasound diagnosis apparatus 1, the following will explain which step in the flowchart corresponds to each of the constituent elements. In the processing procedure illustrated in FIG. 5, some of the steps that are the same as those included in the processing procedure in FIG. 3 will be referred to by using the same reference characters, and details explanations thereof will be omitted. Steps S11 through S19 in FIG. 5 are the same as steps S1 through S9 in FIG. 3. Step S21 in FIG. 5 is the same as step S10 in FIG. 3. At step S11, the input device 102 receives a setting of a plurality of observation-purpose regions of interest. In other words, at step S11, the two or more observation-purpose regions of interest are set.

Step S20 is a step corresponding to the tracking function 182. Step S20 is a step at which the tracking function 182 is realized as a result of the processing circuitry 180 invoking and executing a predetermined program corresponding to the tracking function 182 from the storage circuit 170. At step S17, when the position aligning function 181 determines that the reference structure was not successfully found in the search (step S17: No), the tracking function 182 performs, at step S20, a position aligning process while using the observation-purpose regions of interest as a reference.

FIG. 6 illustrates the plurality of ultrasound images 40 generated in the time series and the electrocardiographic waveform 50. Further, FIG. 6 illustrates the reference image 30 in the CT phase. For example, as illustrated in FIG. 6, at the time T1 in the CT phase, the tracking function 182 sets the observation-purpose regions of interest 40a in the ultrasound image 40, on the basis of the relative positional relationship based on the structure of the heart. After that, at the time of re-setting the observation-purpose regions of interest 40a at the time T2 in the CT phase, when the reference structure is not successfully found in the search and the position aligning process has failed, the tracking function 182 performs a position aligning process between the ultrasound image 40 in the CT phase and the reference image 30, by using the observation-purpose regions of interest 40a. In this situation, the tracking function 182 performs the position aligning process between the ultrasound image 40 in the CT phase and the reference image 30, by using the plurality of observation-purpose regions of interest 40a.

As explained above, the ultrasound diagnosis apparatus 1 according to the second embodiment is configured to perform, in the CT phase, the position aligning process between the reference image and the ultrasound image, to set the observation-purpose regions of interest, and to track the observation-purpose regions of interest in temporal phases other than the CT phase. With this arrangement, according to the second embodiment, even in the temporal phases different from the CT phase, it is possible to observe, in a real-time manner and in synchronization with the movement of the heart, the observation-purpose regions of interest that were set prior to the manipulation.

Further, the ultrasound diagnosis apparatus 1 according to the second embodiment is configured to re-set, in the CT phase, the observation-purpose regions of interest. With this arrangement, according to the second embodiment, it is possible to reset position error, if any, that may be caused by the tracking of the observation-purpose regions of interest.

Further, even when, in the CT phase, the reference structure used as a reference in the position aligning process comes out of the image taking area of the ultrasound image, the ultrasound diagnosis apparatus 1 according to the second embodiment is configured to perform the position aligning process between the ultrasound image in the CT phase and the reference image by using the observation-purpose regions of interest. With this arrangement, according to the second embodiment, even when the reference structure used as a reference in the position aligning process comes out of the image taking area of the ultrasound image, it is possible to perform the position aligning process between the ultrasound image in the CT phase and the reference image.

Third Embodiment

In the first and the second embodiments, the example is explained in which the position aligning process is performed between the reference image and the ultrasound image by recognizing the structure of the heart in the reference image and in the ultrasound image. Incidentally, when a position sensor is attached to the ultrasound probe 101, it is also acceptable to perform a position aligning process between the reference image and the ultrasound image, by using position information of the ultrasound probe 101 obtained by the position sensor. Accordingly, in a third embodiment, an example will be explained in which the position aligning process is performed between the reference image and the ultrasound image, by using the position information of the ultrasound probe 101 obtained by the position sensor. Further, when a position sensor is attached to a TEE probe, the third embodiment is also applicable to an ultrasound scan performed by using the TEE probe.

First, an exemplary configuration of the ultrasound diagnosis apparatus 1a according to the third embodiment will be explained. In the ultrasound diagnosis apparatus 1a according to the third embodiment, some of the constituent elements that are the same as those in the ultrasound diagnosis apparatus 1 according to the first embodiment illustrated in FIG. 1 will be referred to by using the same reference characters, and detailed explanations thereof will be omitted.

FIG. 7 is a block diagram illustrating the exemplary configuration of the ultrasound diagnosis apparatus 1a according to the third embodiment. As illustrated in FIG. 7, the ultrasound diagnosis apparatus 1a according to the third embodiment includes an apparatus main body 100a, the ultrasound probe 101, the input device 102, the display device 103, a position sensor 104, and a transmitter 105. The ultrasound probe 101, the input device 102, the display device 103, and the transmitter 105 are connected to the apparatus main body 100a so as to be able to communicate therewith. Further, the ultrasound diagnosis apparatus 1*a* according to the third embodiment is connected to the electrocardiograph 106.

The position sensor 104 and the transmitter 105 are devices (a position detecting system) used for obtaining the position information of the ultrasound probe 101. For example, the position sensor 104 may be a magnetic sensor attached to the ultrasound probe 101. Further, for example, the transmitter 105 is a device that is disposed in an arbitrary position and is configured to form a magnetic field outwardly so as to be centered thereon.

The position sensor 104 is configured to detect the three-dimensional magnetic field formed by the transmitter 105. Further, on the basis of information about the detected magnetic field, the position sensor 104 is configured to calculate the position (coordinates) and the orientation (an angle) of the position sensor 104 within a space that uses the transmitter 105 as the origin thereof and to further transmit the calculated position and orientation to processing circuitry 180*a*. The three-dimensional position information (the position and the orientation) of the position sensor 104 transmitted to the processing circuitry 180*a* will be used after being converted, as appropriate, into either position information of the ultrasound probe 101 or position information of a scan range scanned by the ultrasound probe 101. For example, the position information of the position sensor 104 is converted into the position information of the ultrasound probe 101, on the basis of a positional relationship between the position sensor 104 and the ultrasound probe 101. Further, the position information of the ultrasound probe 101 is converted into position information of the scan range on the basis of a positional relationship between the ultrasound probe 101 and the scan range. Further, it is also possible to convert the position information of the scan range into pixel positions, on the basis of a positional relationship between the scan range and sample points on scanning lines. In other words, it is possible to convert the three-dimensional position information of the position sensor 104 into the pixel positions of ultrasound image data taken by using the ultrasound probe 101.

The present embodiment is also applicable to situations where the position information of the ultrasound probe 101 is obtained by using a system other than the position detecting system described above. For example, the present embodiment is applicable to situations where the position information of the ultrasound probe 101 is obtained by using a gyro sensor, an acceleration sensor, or the like.

As illustrated in FIG. 7, the apparatus main body 100*a* includes the transmission circuit 110, the reception circuit 120, the B-mode processing circuitry 130, the Doppler processing circuitry 140, the image generating circuit 150, the image memory 160, the storage circuit 170, the processing circuitry 180*a*, and a communication interface 190. The transmission circuit 110, the reception circuit 120, the B-mode processing circuitry 130, the Doppler processing circuitry 140, the image generating circuit 150, the image memory 160, the storage circuit 170, the processing circuitry 180*a*, and the communication interface 190 are connected so as to be able to communicate with one another. Further, the apparatus main body 100*a* is connected to a network 5.

The communication interface 190 is an interface used for communicating with any of various types of apparatuses provided in the hospital via the network 5. By using the communication interface 190, the processing circuitry 180*a* is configured to communicate with an external apparatus. For example, the processing circuitry 180*a* is configured to receive medical image data (e.g., X-ray Computed Tomography [CT] image data, Magnetic Resonance Imaging [MRI] image data) taken by a medical image diagnosis apparatus other than the ultrasound diagnosis apparatus 1*a*, via the network 5.

Every time an ultrasound image satisfying a predetermined condition is generated by the image generating circuit 150, a position aligning function 181*a* according to the third embodiment is configured to perform a position aligning process between the ultrasound image satisfying the predetermined condition and a reference image obtained in advance. In this situation, the position aligning function 181*a* according to the third embodiment performs the position aligning process between the ultrasound image satisfying the predetermined condition and the reference image, by using the position information of the ultrasound probe 101 obtained from the position sensor 104.

A tracking function 182*a* according to the third embodiment is configured to identify, within the ultrasound image satisfying the predetermined condition, an observation-purpose region of interest set in the reference image, on the basis of a result of the position aligning process. Further, the tracking function 182*a* according to the third embodiment is configured to track the observation-purpose region of interest in ultrasound images in a time series that are newly generated by the image generating circuit 150 during or after the position aligning process.

Next, a processing procedure performed by the ultrasound diagnosis apparatus 1*a* according to the third embodiment will be explained. FIG. 8 is a flowchart illustrating the processing procedure performed by the ultrasound diagnosis apparatus 1*a* according to the third embodiment. With reference to FIG. 8, while the flowchart explains an operation performed by the entirety of the ultrasound diagnosis apparatus 1*a*, the following will explain which step in the flowchart corresponds to each of the constituent elements. In the processing procedure illustrated in FIG. 8, some of the steps that are the same as those included in the processing procedure in FIG. 3 will be referred to by using the same reference characters, and details explanations thereof will be omitted. Steps S31 through S35 in FIG. 8 are the same as steps S1 through S5 in FIG. 3. Steps S38 through S40 in FIG. 8 are the same as steps S8 through S10 in FIG. 3.

Steps S36 and S37 are steps corresponding to the position aligning function 181*a*. Steps S36 and S37 are steps at which the position aligning function 181*a* is realized as a result of the processing circuitry 180*a* invoking and executing a predetermined program corresponding to the position aligning function 181*a* from the storage circuit 170. When having determined that the temporal phase of the ultrasound image obtained at step S34 is the CT phage, the position aligning function 181*a* obtains position information at step S36. For example, the position aligning function 181*a* obtains the three-dimensional position information calculated by the position sensor 104.

At step S37, the position aligning function 181*a* performs a position aligning process between the ultrasound image and the reference image. For example, by using the position information obtained at step S36, the position aligning function 181*a* performs the position aligning process between the ultrasound image and the reference image. The position aligning function 181*a* converts the position information obtained at step S36 into pixel positions of the ultrasound image taken by using the ultrasound probe 101. Subsequently, the position aligning function 181*a* sets a position-aligning-purpose reference region within the reference image and further performs a position aligning process between pixel positions of the position-aligning-purpose reference region within the reference image and the pixel positions of the ultrasound image.

In this manner, the ultrasound diagnosis apparatus 1a according to the third embodiment performs, in the CT phase, the position aligning process between the reference image and the ultrasound image and sets an observation-purpose region of interest (step S38) and further tracks the observation-purpose region of interest in temporal phases other than the CT phase (step S39). With these arrangements, according to the third embodiment, even in the temporal phases different from the CT phase, it is possible to observe, in a real-time manner and in synchronization with the movement of the heart, the observation-purpose region of interest that was set prior to the manipulation.

Further, the ultrasound diagnosis apparatus 1a according to the third embodiment is configured to re-set, in the CT phase, the observation-purpose region of interest. With this arrangement, according to the third embodiment, it is possible to reset position error, if any, that may be caused by the tracking of the observation-purpose region of interest.

Further, when, in the CT phase, the reference structure used as a reference in the position aligning process comes out of the image taking area of the ultrasound image, the ultrasound diagnosis apparatus 1a according to the third embodiment may track the observation-purpose region of interest, without performing the position aligning process.

Further, when, in the CT phase, the reference structure used as a reference in the position aligning process comes out of the image taking area of the ultrasound image and it is not possible to perform the position aligning process between the reference image and the ultrasound image, the ultrasound diagnosis apparatus 1a according to the third embodiment may perform the position aligning process between the ultrasound image and the reference image by using the observation-purpose region of interest.

Other Embodiments

Possible embodiments are not limited to the embodiments described above.

In the embodiments described above, the example is explained in which, every time an ultrasound image in the CT phase is generated for each heartbeat, the position aligning function 181 performs the position aligning process between the ultrasound image and the reference image obtained in advance; however possible embodiments are not limited to this example. For instance, the position aligning function 181 may perform the position aligning process between the ultrasound image and the reference image by using a plurality of heartbeats as one cycle. In one example, every time an ultrasound image in the CT phase corresponding to two heartbeats is generated, the position aligning function 181 may perform the position aligning process between the ultrasound image and the reference image.

Further, in the embodiments described above, the example is explained in which the observation-purpose region of interest is expressed with a circular shape including a single point of interest in the patient's body; however, possible embodiments are not limited to this example. For instance, the observation-purpose region of interest may be expressed with a straight line or a circular shape used in a measuring process or the like or may be expressed with a line used as a guide indicating a path for passage of a catheter that was planned prior to the manipulation.

Further, in the embodiments described above, the example is explained in which the position-aligning-purpose reference region and the observation-purpose region of interest are set in mutually-different regions; however, possible embodiments are not limited to this example. For instance, when the observation-purpose region of interest is a structure, it is also acceptable to set the position-aligning-purpose reference region and the observation-purpose region of interest in mutually the same region.

Further, in the embodiments described above, the example is explained in which the position aligning function 181 sets the position-aligning-purpose reference region; however, possible embodiments are not limited to this example. For instance, the position aligning function 181 may receive, from the operator, a setting of a position-aligning-purpose reference region within the reference image, via the input device 102. In that situation, by using the position-aligning-purpose reference region received from the operator, the position aligning function 181 performs the position aligning process between the ultrasound image and the reference image.

Further, the number of observation-purpose regions of interest and the number of position-aligning-purpose reference regions that are set by the ultrasound diagnosis apparatuses 1 and 1a as described above may arbitrarily be changed. Further, when two or more position-aligning-purpose reference regions are set, the ultrasound diagnosis apparatuses 1 and 1a may perform the position aligning process by using the two or more position-aligning-purpose reference regions, whereas the display device 103 displays one of the plurality of position-aligning-purpose reference regions.

Further, in the embodiments described above, the example is explained in which the position aligning process is performed between the two-dimensional reference image and the two-dimensional ultrasound image, and the region of interest is set; however possible embodiments are not limited to this example. For instance, the ultrasound diagnosis apparatuses 1 and 1a according to the embodiments may perform a position aligning process between a three-dimensional reference image and a three-dimensional ultrasound image and further set an observation-purpose region of interest.

Further, in the embodiments described above, the ultrasound scan performed on the heart is used as an example; however, possible embodiments are not limited to this example. For instance, the embodiments described above are applicable to an ultrasound scan performed on the head, the chest, the abdomen, and the like, besides the heart.

Further, in the embodiment described above, the observation target involving periodical movement such as the heart is used as an example; however, possible embodiments are not limited to this example. For instance, the embodiments described above are also applicable to an observation target involving non-periodical movement (e.g., intestinal peristalsis). In that situation, the ultrasound diagnosis apparatuses 1 and 1a are configured to perform a position aligning process between a reference image taken in a predetermined temporal phase and an ultrasound image taken in the predetermined temporal phase that arrives non-periodically and to set an observation-purpose region of interest. After that, the ultrasound diagnosis apparatuses 1 and 1a according to the embodiments are configured to track the observation-purpose region of interest in temporal phases other than the predetermined temporal phase.

The term "processor" used in the explanations above denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions thereof by reading and executing programs saved in a storage circuit. In this situation, instead of saving the programs in the storage circuit, it is also acceptable to directly incorporate the programs in the circuits of the processors. In that situation, the processors realize the functions thereof by reading and executing the programs incorporated in the circuits thereof. Further, the processors in the present embodiments do not each necessarily have to be structured as a single circuit. It is also acceptable to structure one processor by combining together a plurality of independent circuits so as to realize the functions thereof. Further, it is also acceptable to integrate two or more of the constituent elements illustrated in FIG. 1 into one processor so as to realize the functions thereof.

The constituent elements of the apparatuses and the devices illustrated in the drawings used in the explanations of the embodiments above are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program that is analyzed and executed by the CPU or may be realized as hardware using wired logic.

Further, the controlling method explained in the above embodiments may be realized by causing a computer such as a personal computer or a workstation to execute a control program prepared in advance. The control program may be distributed via a network such as the Internet. Further, the control program may be recorded on a computer-readable recording medium such as a hard disk, a flexible disk (FD), Compact Disk Read-Only Memory (CD-ROM), a Magneto-Optical (MO) disk, or a Digital Versatile Disk (DVD), so as to be executed as being read from the recording medium by a computer.

According to at least one aspect of the embodiments described above, it is possible to accurately display the observation target that involves movement.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising processing circuitry configured:
    to generate ultrasound images in a time series on a basis of data acquired by transmitting and receiving an ultrasound wave;
    to perform, every time an ultrasound image satisfying a predetermined condition is generated, a position aligning process between the ultrasound image satisfying the predetermined condition and a reference image obtained in advance; and
    to identify, within the ultrasound image satisfying the predetermined condition, a region of interest set in the reference image, on a basis of a result of the position aligning process and to track the region of interest in ultrasound images in a time series that are newly generated during or after the position aligning process, wherein
    the processing circuitry performs the position aligning process between the ultrasound image satisfying the predetermined condition and the reference image by searching for a reference structure included in the reference image from the ultrasound image satisfying the predetermined condition, the reference structure being positioned at a region which is different from the region of interest set in the reference image.

2. The ultrasound diagnosis apparatus according to claim 1, wherein, when the reference structure is not successfully found in the searching, the processing circuitry keeps tracking the region of interest in the ultrasound images in the time series that are newly generated during or after the position aligning process.

3. The ultrasound diagnosis apparatus according to claim 1, wherein, when the reference structure is not successfully found in the searching, the processing circuitry performs the position aligning process between the ultrasound image satisfying the predetermined condition and the reference image, by using the region of interest.

4. The ultrasound diagnosis apparatus according to claim 3, wherein
    two or more of the regions of interest are set, and
    the processing circuitry performs the position aligning process between the ultrasound image satisfying the predetermined condition and the reference image, by using the two or more regions of interest.

5. The ultrasound diagnosis apparatus according to claim 1, further comprising: a position sensor configured to obtain position information of an ultrasound probe, wherein
    the processing circuitry performs the position aligning process between the ultrasound image satisfying the predetermined condition and the reference image, by using the position information of the ultrasound probe obtained from the position sensor.

6. The ultrasound diagnosis apparatus according to claim 1, wherein the ultrasound image satisfying the predetermined condition is an ultrasound image corresponding to a periodical reference temporal phase.

7. The ultrasound diagnosis apparatus according to claim 6, wherein the periodical reference temporal phase is a temporal phase in which the reference image was taken.

8. An ultrasound diagnosis apparatus controlling method comprising:
    generating ultrasound images in a time series on a basis of data acquired by transmitting and receiving an ultrasound wave;
    performing, every time an ultrasound image satisfying a predetermined condition is generated, a position aligning process between the ultrasound image satisfying the predetermined condition and a reference image obtained in advance; and
    identifying, within the ultrasound image satisfying the predetermined condition, a region of interest set in the reference image, on a basis of a result of the position aligning process and tracking the region of interest in ultrasound images that are among ultrasound images in a time series newly generated during or after a most recent position aligning process and are other than the ultrasound image satisfying the predetermined condition, wherein the performing comprises performing the position aligning process between the ultrasound image satisfying the predetermined condition and the reference image by searching for a reference structure included in the reference image from the ultrasound image satisfying the predetermined condition, the reference structure being positioned at a region which is different from the region of interest set in the reference image.

9. The ultrasound diagnosis apparatus according to claim 1, wherein the reference structure is a valve annulus or the left auricle.

* * * * *